US006570999B1

(12) United States Patent
Monson

(10) Patent No.: US 6,570,999 B1
(45) Date of Patent: May 27, 2003

(54) SOIL PARTICLE AND SOIL ANALYSIS SYSTEM

(75) Inventor: Robert J. Monson, St. Paul, MN (US)

(73) Assignee: Ag-Chem Equipment Co., Inc., Minnetonka, MN (US)

( * ) Notice: Subject to any disclaimer, the term of this patent is extended or adjusted under 35 U.S.C. 154(b) by 0 days.

(21) Appl. No.: 09/313,154

(22) Filed: May 17, 1999

Related U.S. Application Data

(60) Provisional application No. 60/096,821, filed on Aug. 17, 1998.

(51) Int. Cl.$^7$ ................................................. G06K 9/00
(52) U.S. Cl. ....................... 382/109; 356/335; 356/340; 356/239.8; 324/71.1
(58) Field of Search ................................ 382/100, 109, 382/108, 203; 356/335, 336, 338, 340, 239.8, 237.3; 324/71.1, 71.3, 332; 702/2

(56) References Cited

U.S. PATENT DOCUMENTS

| | | | |
|---|---|---|---|
| 3,464,504 A | 9/1969 | Stange | 173/28 |
| 3,593,809 A | 7/1971 | Derry | 175/51 |
| 4,266,878 A | 5/1981 | Auer | 356/419 |
| 4,284,150 A | 8/1981 | Davis | 175/84 |
| 4,332,301 A | 6/1982 | Jonell | 175/50 |
| 4,333,541 A | 6/1982 | Doty | 175/162 |
| 4,482,021 A | 11/1984 | Repski | 175/209 |
| 4,630,773 A | 12/1986 | Ortlip | 239/1 |
| 4,685,339 A | 8/1987 | Philipenko | 73/864.45 |

(List continued on next page.)

FOREIGN PATENT DOCUMENTS

| | | |
|---|---|---|
| WO | WO 95/04450 | 2/1995 |
| WO | WO 95/04870 | 2/1995 |
| WO | WO 96/04553 | 2/1996 |

OTHER PUBLICATIONS

New Tool Prescribes Precise Nitrogen Needs; Grant Mangold; *Soybean Digest Feb. 1988*.
Sensors Utilizing Light Reflection to Measure Soil Organic Matter; M. Pitts, J. Hummel, B. Butler; *American Society of Agricultural Engineers*.
Undercover Light 'Reads' Soil Organic Level; *Successful Farming, Planning Issue Nov., 1987*.
Close–Range Sensing of Soil Organic Matter; P. Krishman, B. J. Butler, J. Hummel; *Transactions of the ASAE—1981*.
Spectroscopic Sensing for the Determination of Organic Matter Contest; J. Shonk, L. Gaultney; *American Society of Agricultural Engineers—Jun. 1988*.
Derivative Sensor, author unknown, pp. 7–11, 13–19, Figures 1, 3–10.
Automated Nitrate Monitoring System; Nova Scotia Agricultural College; Department of Agricultural Engineering.
Test Your Soil For Acidity; C.M. Lindsley and F.C. Bauer; University of Illinois College of Agriculture and Agricultural Experiment Station; Circular 346.
Chromatography; Richard Villalobos; Beckman Instruments, Inc., Fullerton, CA.

(List continued on next page.)

*Primary Examiner*—Timothy M. Johnson
*Assistant Examiner*—Sheela Chawan
(74) *Attorney, Agent, or Firm*—Gerald R. Boss; Ryan A. Schneider; Troutman Sanders LLP

(57) ABSTRACT

A soil analysis system for determining one or more categories of soil based upon the particle sizes in a soil sample. The soil analysis system includes an image sensor and an image analysis assembly. The image sensor produces an image to distinguish individual particles of a soil sample and calculates particle size. The image analysis assembly is coupled to the image sensor to determine a category for each particle based upon the size of the particles, percentage of each category of particles, and one or more categories of soil for the soil sample.

22 Claims, 12 Drawing Sheets

U.S. PATENT DOCUMENTS

| | | | |
|---|---|---|---|
| 4,828,047 A | | 5/1989 | Rogerson ..................... 173/24 |
| 4,998,590 A | | 3/1991 | Wells ......................... 175/162 |
| 5,033,397 A | | 7/1991 | Colburn, Jr. ................. 111/118 |
| 5,038,040 A | * | 8/1991 | Funk et al. ............ 250/339.02 |
| 5,044,756 A | | 9/1991 | Gaultney et al. ........... 356/446 |
| 5,076,372 A | | 12/1991 | Hellbusch ..................... 175/20 |
| 5,129,268 A | * | 7/1992 | Uesugi et al. ............. 382/109 |
| 5,213,169 A | | 5/1993 | Heller ........................ 175/122 |
| 5,246,862 A | * | 9/1993 | Grey et al. ................... 436/28 |
| 5,298,139 A | | 3/1994 | Huang et al. ............... 204/299 |
| 5,310,462 A | | 5/1994 | Chen ....................... 204/180.1 |
| 5,316,950 A | * | 5/1994 | Apitz et al. ............. 422/82.07 |
| 5,332,480 A | | 7/1994 | Datta et al. ............... 204/180.1 |
| 5,349,624 A | * | 9/1994 | Warren et al. ................ 378/43 |
| 5,355,815 A | * | 10/1994 | Monson ..................... 111/200 |
| 5,366,601 A | | 11/1994 | Jones et al. ............. 204/180.1 |
| 5,461,229 A | | 10/1995 | Sauter et al. ............... 250/253 |
| RE35,100 E | | 11/1995 | Monson et al. ............ 111/130 |
| 5,467,271 A | | 11/1995 | Abel et al. .................. 364/420 |
| 5,548,115 A | | 8/1996 | Ballard et al. ............. 250/253 |
| 5,561,516 A | | 10/1996 | Noble et al. ................ 250/255 |
| 5,579,409 A | * | 11/1996 | Vaidyanathan et al. ..... 382/203 |
| 5,587,538 A | | 12/1996 | Bratton ................... 73/864.74 |
| 5,668,719 A | * | 9/1997 | Bobrov et al. ................. 702/2 |
| 5,768,128 A | * | 6/1998 | Thompson et al. ............ 702/2 |
| 5,870,686 A | | 2/1999 | Monson ......................... 701/1 |
| 5,883,830 A | | 3/1999 | Hirt et al. ............. 365/185.03 |
| 5,887,686 A | | 3/1999 | Tanaka et al. ................ 701/1 |
| 6,038,026 A | * | 3/2000 | Maris ......................... 356/514 |
| 6,100,526 A | * | 8/2000 | Mayes .................. 250/339.11 |

OTHER PUBLICATIONS

Reflection of Radiant Energy from Soils; S.A. Bowers and R. J. Hanks; *Soil Science*; vol. 100, No. 2.

Spectrophotometric Measurements of Soil Color and Its Relationship to Moisture and Organic Matter; J. A. Shields, E. A. Paul, R. J. St. Arnaud and W. K. Head; Saskatchewan Institute of Pedology, University of Saskatchewan, Saskatoon.

Maximize Dynamic Range in CCD–based Imaging Systems; Steve Ruscak, Analog Devices Inc., EDN, Oct. 27, 1994, pp. 101–108.

CCDS Let You Design Vision into Applications, John Gallant, EDN, Oct. 12, 1995, pp. 87–93.

Photonic Image Processing, pp. 305–309.

Referenced Data for Engineers, pp. 16–34 through 16–38.

Color, Organic Matter, and Pesticides Adsorption Relationships in a Soil Landscape; R. N. Fernandez, D. G. Schulze, D. L. Coffin, and G. E. Van Scoyoc; Contribution From the Agronomy Dept., Purdue University, Univ., Agric.,.Exp.,. Stn., West Lafayette, Indiana 47907; Journal Article No. 11,140.

Biological and Physical Considerations in Applying Computer–Aided Analysis Techniques to Remove Sensor Data; Roger M. Hoffer; Remote Sensing: *The Quantitative Approach*.

Article by Carl L. Griffis; 1985 American Society of Agricultural Engineers 0001–2351/85 p. 703, May–Jun., 1985.

\* cited by examiner

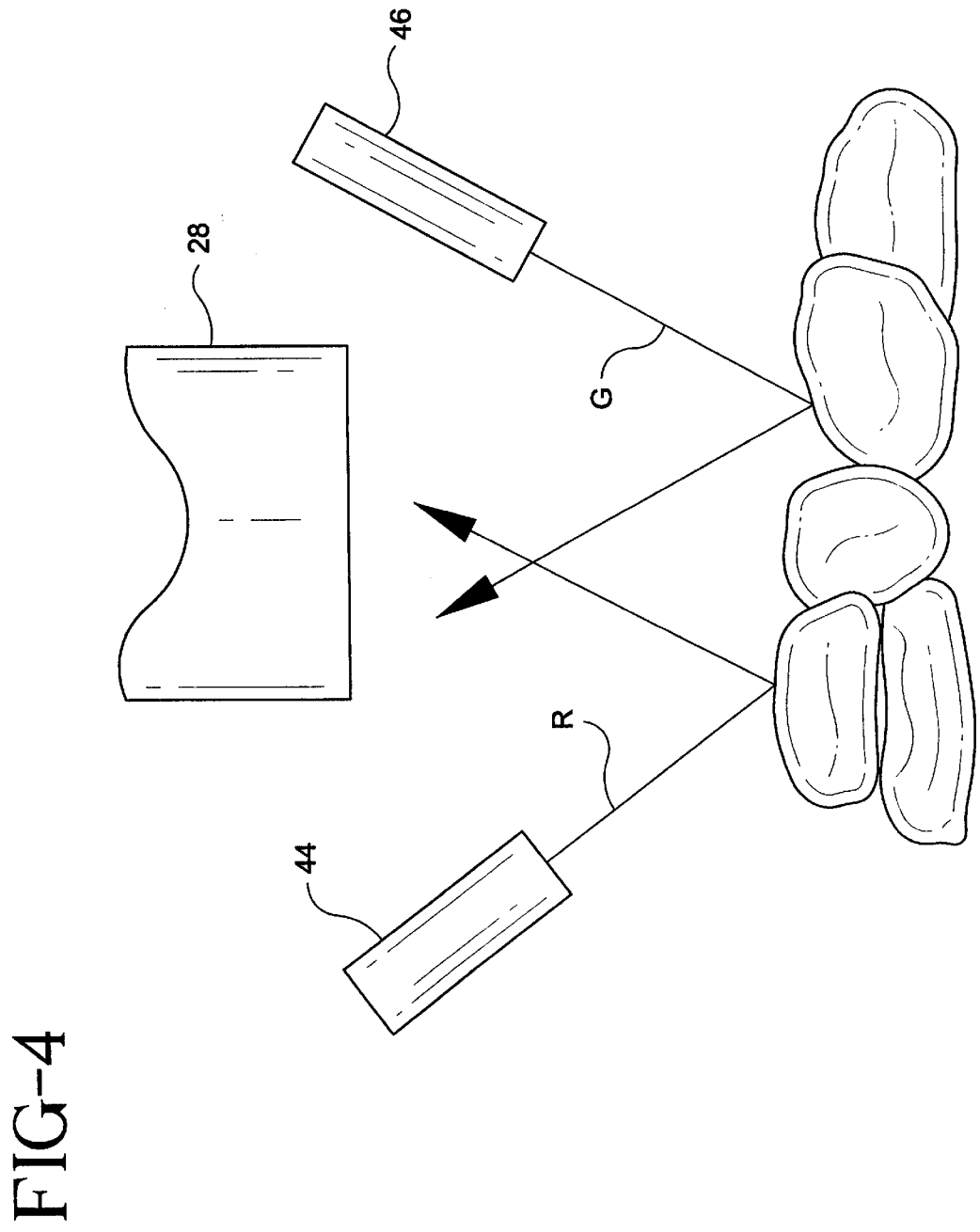

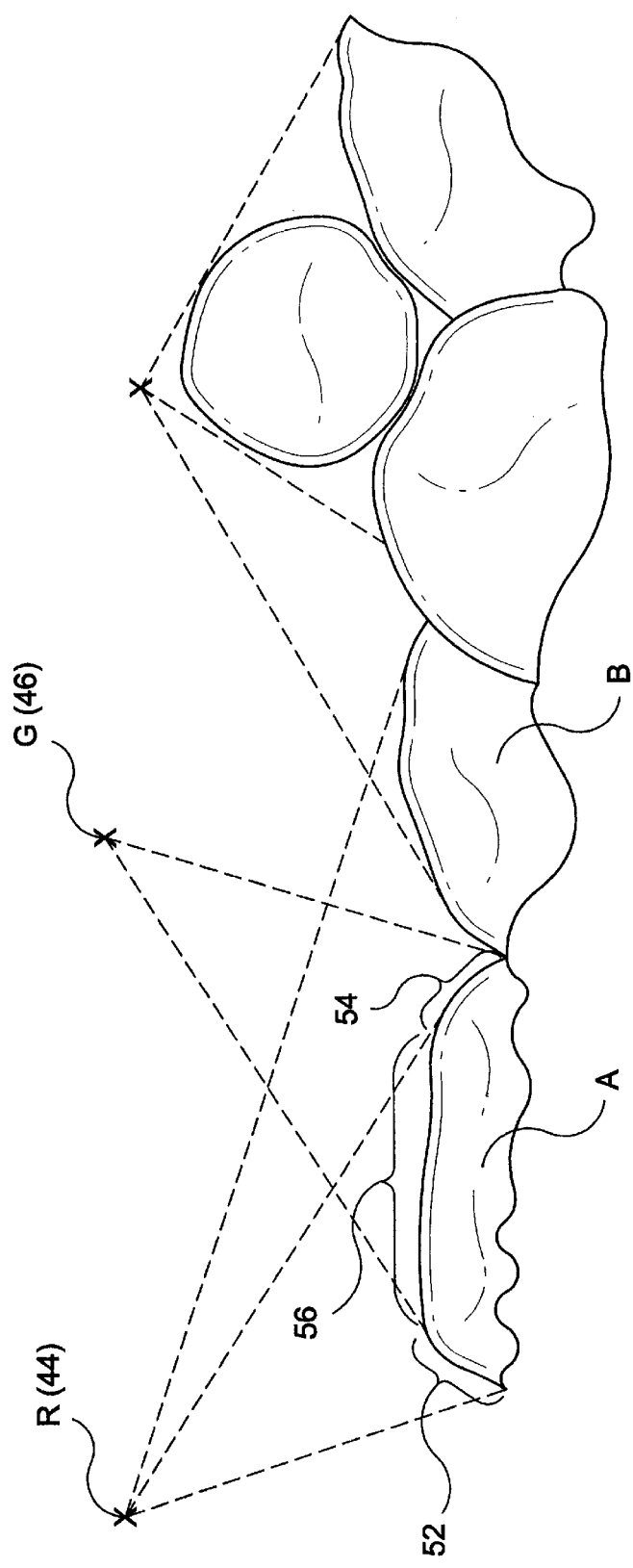

FIG-6A

| R | G | RESULT |
|---|---|--------|
| 126 | 128 | G |
| 129 | 130 | M |
| 140 | 106 | R |
| ... | ... | ... |
| 126 | 127 | N |

THRESHOLD = 128

FIG-6C

| R | G | B | RESULT |
|---|---|---|--------|
| 26 | 128 | 45 | G |
| 26 | 124 | 145 | B |
| 128 | 128 | 45 | M |
| 130 | 126 | 124 | R |
| 135 | 130 | 130 | M |

THRESHOLD = 128

SOIL PARTICLE AND SOIL ANALYSIS SYSTEM

This application claims the benefit of provisional applications Ser. No. 60/096,821, filed Aug. 17, 1990.

BACKGROUND OF THE INVENTION

The present invention relates to a system for determining a soil characteristic, in particular, a system for analysis of the size of individual particles to determine characteristics of soil samples over a geographic area for agricultural applications.

An agricultural field generally includes a variety of soil characteristics. It is particularly useful to evaluate the soil to determine the optimum crops for maximum yield potential and for treatment methods available.

Reference is made to U.S. Pat. No. 4,630,773, entitled, Method and Apparatus for Spreading Fertilizer; U.S. Pat. No. 5,355,815, entitled, Closed-Loop Variable Rate Applicator; and U.S. Pat. No. 5,887,491, entitled, Soil Analysis Assembly and System.

All documents cited herein, including the foregoing, are incorporated herein by reference in their entireties for all purposes.

SUMMARY OF THE INVENTION

The present invention relates to a soil analysis system for determining: 1) a percentage of particles within certain size ranges in a region of interest in a soil sample, for example, size ranges comparable to sand, silt, and clay; and 2) a general soil characterization of the soil sample as a function of the percentage of the particles in each size range.

Although soil type can include particular characteristics such as the physical nature of the soil, e.g., average particle size of sand, silt, clay, and the like, and their respective relationships, a general reference to the term soil type can include a variety of other characteristics and properties of a soil sample.

The soil analysis apparatus determines a particular soil characteristic of a soil sample, in particular, the general physical nature of particles and the percentage of particles having generally common physical features. The soil analysis system is configured to determine a soil sample as one of generally sand, silt, clay, sandy clay, silty clay, sandy clay loam, clay loam, silty clay loam, loamy sand, sandy loam, loam, and the like.

With the soil analysis system, a series of soil samples can be analyzed to advantageously determine the relative soil makeup over a geographic area. Sand, silt, and clay each have a generally distinct size range relative to one another and their respective percentage in a soil sample can determine a general soil character. For example, sand is generally characterized by large particle size; silt by medium particle size; and clay by small particle size. The relationship of each soil sample to another can be used to map soil characteristics over a geographic area.

The soil analysis system includes an image analysis assembly coupled to an image sensor to isolate particles and calculate individual particle size to advantageously determine characteristics of a plurality of soil samples throughout a geographic area. The soil information may be further analyzed to determine a treatment plan as a function of the soil characteristics and the respective location of each soil sample in a geographical area.

In sum, the invention relates to a soil analysis system. The soil analysis system includes a sensor device and an image analysis assembly. The sensor device produces information corresponding to an image of at least a portion of one or more particles in one or more portions of a soil sample. The image analysis assembly is operatively coupled to the sensor device and determines a category for each of the one or more particles. The category is based on a function of size or surface area of each particle. The soil analysis system may determine a category for the one or more portions of the soil sample. The category may include clay, sandy clay, silty clay, sandy clay loam, clay loam, silty clay loam, sand, loamy sand, sandy loam, loam, and silt. The image analysis assembly may further include a particle size calculation assembly for determining the size of the one or more particles and a soil determination assembly for determining at least one category of soil. The soil analysis system may further include a first light source positioned at an angle relative to the soil sample on a first side of the sensor device and a second light source positioned at an angle relative to the soil sample on a second side of the sensor device. The first light source may have a first wavelength and the second light source may have a second wavelength different from the first wavelength. The sensor device may distinguish at least a portion of one or more edges of the one or more particles. The particle size calculation assembly may determine an average radius of the one or more particles. The image analysis assembly may determine if a particle has been substantially isolated. The image analysis assembly may compare the size of the one or more particles in the soil sample to data relating to sand, silt, and clay and categorize the one or more particles as one of sand, silt, and clay. The image analysis assembly may determine the percentage of sand, silt, and clay in the soil sample and categorize the soil sample. The image analysis assembly may be operatively coupled to a controller for operation of an apparatus for treatment of a geographic area. The image analysis assembly may be operatively coupled to a mapping system. The image analysis assembly may be operatively coupled to a map analysis system for analyzing one or more data maps. The mapping system may integrate one or more soil type maps with one or more data maps. The controller may functionally cooperate with one or more maps relating to characteristics of a geographic area.

The invention also relates to a soil imaging assembly including a sensor device and a soil image assembly. The sensor device produces at least one form of an image corresponding to one or more portions of a soil sample including a plurality of particles. The sensor device has sufficient resolution to distinguish the plurality of particles. The soil image assembly functionally cooperates with the image sensor. The image sensor and the soil image assembly communicate with one another to determine at least one of: a) one or more categories of particles in the soil sample; b) a percentage of each category of particle in the soil sample; and c) a category of soil representative of the percentages of the one or more categories of particles in the soil sample. The sensor device may include a photosensitive imaging device. The photosensitive imaging device may include a charged coupled device. The charged coupled device may includes color capability. The soil imaging assembly may further include a first and second light source. Each light source has one or more wavelengths corresponding to at least one of red, green, and blue.

The invention also relates to a method for analyzing soil including: positioning a photosensitive imaging device adapted to convert light intensity to an image in a functional relationship with one or more portions of a soil sample, the soil sample including one or more particles; producing information corresponding to an image of at least a portion of the one or more particles; isolating at least a portion of the one or more particles; calculating a size of the one or more particles; comparing the size of the one or more particles to data relating to at least one of sand, silt, and clay; classifying the one or more particles as one of sand, silt, and clay; determining the percentage of the sand, silt, and clay in the one or more portions of the soil sample; comparing the percentages of the sand, silt, and clay to data relating to at least one category of soil; and classifying the one or more portions of the soil sample as at least one of clay, sandy clay, silty clay, sandy clay loam, clay loam, silty clay loam, sand, loamy sand, sandy loam, loam, and silt.

Still other objects and advantages of the present invention and methods of construction of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction, and its several details are capable of modification in various obvious respects, all without departing from the invention. Accordingly, the drawing and description are to be regarded as illustrative in nature, and not as restrictive.

BRIEF DESCRIPTION OF THE DRAWINGS

FIG. 4 is a plan view of enlarged individual particles at the soil surface of FIG. 3 and a sensor device;

FIG. 5 is a schematic view of exposed surfaces of adjacent particles and a sensor device;

FIG. 6A is a simplified example of data storage corresponding to measurements of light intensity of individual particles;

FIG. 6C is a simplified example of data storage corresponding to measurements of light intensity of individual particles;

DESCRIPTION OF THE PREFERRED EMBODIMENTS

The present invention relates to a soil analysis system for determining soil characteristics over a geographic area based upon an analysis of particle size in a plurality of soil samples. The soil samples are imaged at spaced intervals to create a detailed description of the soil over a geographic area. The information may be used to determine optimum plant varieties for maximum yield and treatment plans for crop growth.

Figure 1:
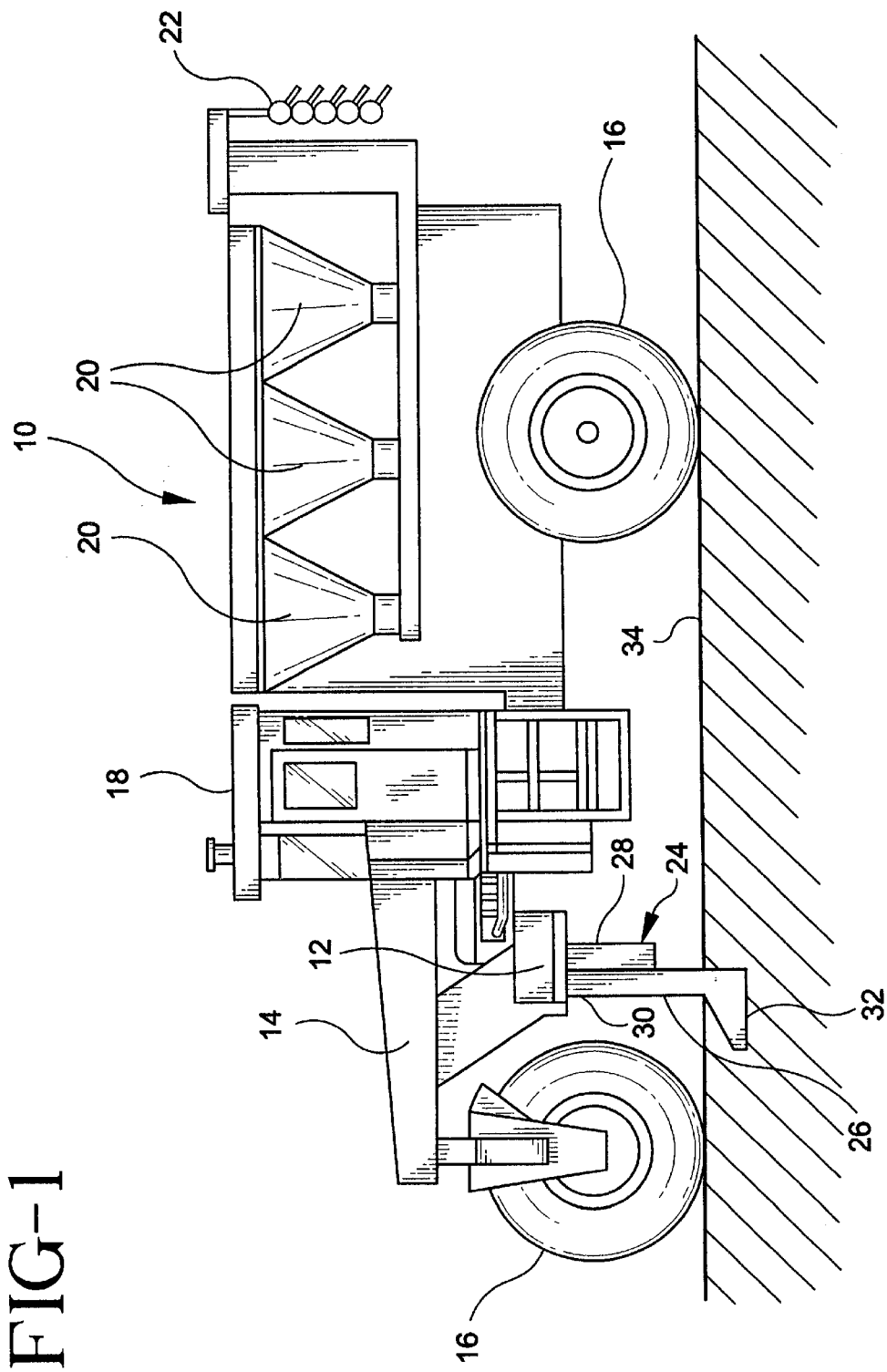
FIG. 1 is a side elevation view of a vehicle including the soil particle and soil analysis system.
Figure 2:
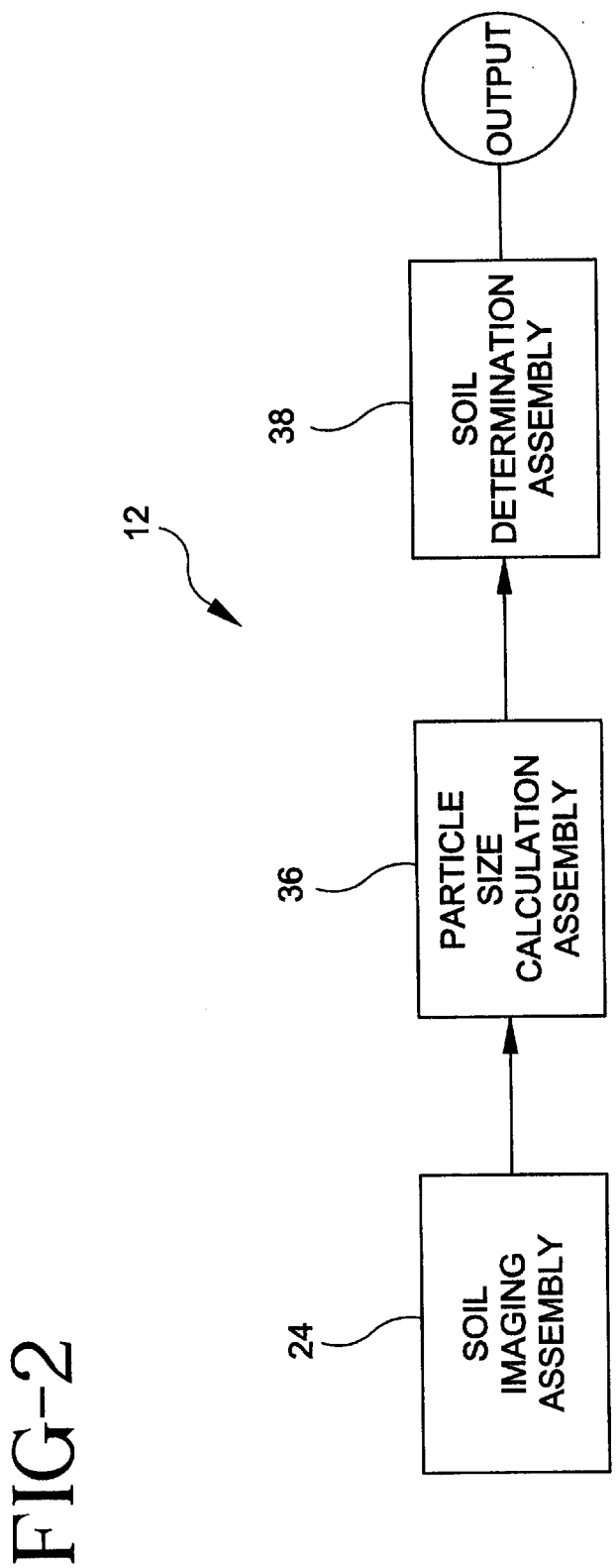
FIG. 2 is a simplified block diagram of components of the soil particle and soil analysis system.

Reference is made to FIGS. 1–2 which illustrates a vehicle 10 including a soil analysis system 12, frame 14, wheels 16, cab 18, hoppers 20, and dispensing apparatus 22. The soil analysis system 12 includes a soil imaging assembly 24, particle size calculation assembly 36, and soil determination assembly 38. The soil imaging assembly 24 captures an image of a soil sample and distinguishes individual particles in the soil sample. Generally, the particles are arranged in a non-uniform pattern and include curved surfaces. The particle size calculation assembly 36 analyzes the size of the individual particles in the soil sample. The soil determination assembly 38 compares the size of the individual particles to particle size data and determines each particle characteristic as one of sand, silt, and clay; calculates a percentage of sand, silt, and clay in the soil sample; and compares the percentage of sand, silt, and clay to soil data to determine a category of soil for the soil sample.

The soil imaging assembly 24 includes a knife 26 and an image sensor 28. The knife 26 includes a base 30 coupled to the frame 14, and a knife extension 32. In use, the knife extension 32 engages and uncovers a layer of soil at a depth between about 1 to about 8 inches below a soil surface 34 to obtain a generally static soil sample. A housing structure may enclose the image sensor 28 and light sources to block or reduce the influence of ambient light. The soil imaging assembly 24 may incorporate a probe structure adjustable supported relative to frame 14 for insertion into the ground to image a soil sample. The probe structure may be used for collection of soil samples for further analysis.

In use, the vehicle 10 transverses a field as the soil imaging assembly 24 images a plurality of soil samples at spaced intervals. A controller coupled to an output such as the dispensing apparatus 22 may dispense material at selected rates from hoppers 20. The soil analysis system 12 may be used with a testing vehicle for collection and analysis of soil data.

Figure 3:
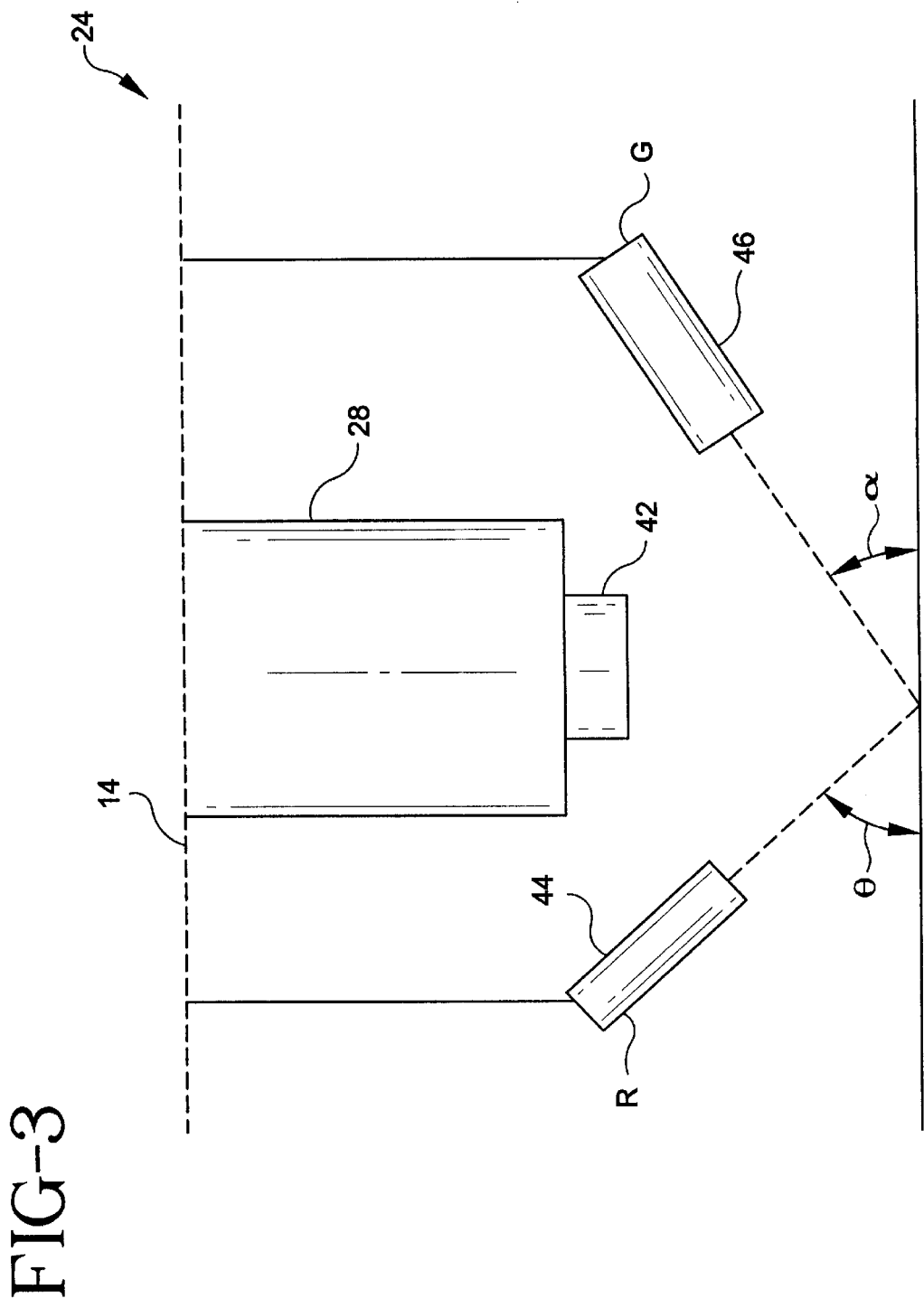
FIG. 3 is a plan view of an image sensor over a soil surface.

FIGS. 3–4 illustrate an embodiment of a soil imaging assembly 24 including an image sensor 28, microscopic lens 42, first light source 44, and second light source 46 for imaging a soil sample. Preferably, the image sensor 28 is a camera including a color charge coupled device (CCD) and a focus lens positioned generally perpendicular to the subject soil sample. The first light source 44 is located on a first side of the image sensor 28, at an angle θ, preferably about 45 degrees relative to the soil sample. The second light source 46 is located on a second opposed side of the image sensor 28, at an angle , preferably about 45 degrees relative to the soil sample. Alternatively, the image sensor 28 and light sources 44, 46 may be positioned at angles less than 90 degrees relative to the soil sample, sufficient to obtain images and relationships of the particles at the image sensor 28.

Light sources. 44, 46 provide distinguishable wavelengths for identifying the individual particles in the soil sample. Preferably, the light sources 44, 46 are coherent collimated light corresponding to at least two of the primary colors of light: red, green and blue. In a preferred embodiment, light source 44 is a red light source and light source 46 is a green light source. Light sources 44, 46 cooperate with the image sensor 28 sufficiently to distinguish at least the exposed surfaces, provides an edge enhanced view of the individual particles, and produces a color image. Other colored light sources and wavelengths may be used to distinguish the particles.

As shown in FIG. 5, red and green light from respective light sources 44, 46 reflect from the exposed surfaces of the individual particles and are received at the image sensor 28 to create an image. For example, particle A includes surface areas with red light portion 52, green light portion 54 and a mixed red/green light portion 56. The image sensor 28 receives a red image R from red light portion 52, a green image G from green light portion 54, and a red/green image M from the mixed light portion 56. The resulting light portions 52, 54 and 56 relate to the orientation of the exposed surfaces and the light sources 44, 46. The size and orientation of the particles, and the spatial relationship between the light sources 44, 46, image sensor 28, and the particles influence the resulting image at the image sensor 28.

Figure 9:
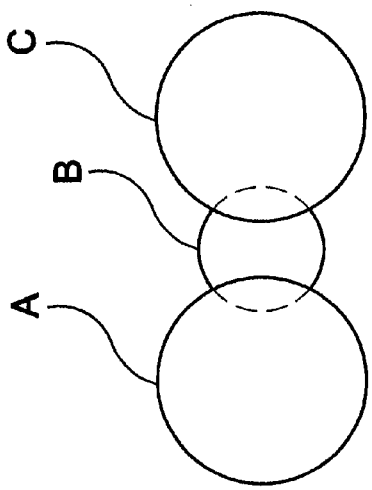
FIG. 9 is a plan view of a particle partially hidden behind other particles.
Figure 8:
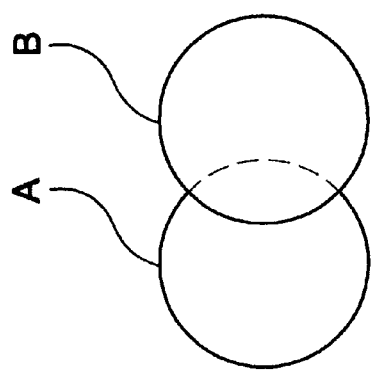
FIG. 8 is a plan view of overlapping particles.

The image sensor 28 outputs data to a computer to determine particle size. The data and software can create three dimensional information to determine the size and relationships of the particles. For example, the length of a shadow and angles of light source can determine the height of a particle when a portion of the particle is hidden or obstructed as shown in FIGS. 8–9.

Image sensor 28 preferably includes an area array with photosensitive MOS capacitors formed into a two dimensional matrix. Pixels including optical microlens focus the light onto the capacitors. The photosensitive elements convert light from an image into an electrical charge. The image sensor 28 includes an output that converts the charge into voltage and provides a pixel-by-pixel, row by row representation of the image on the area array.

FIG. 6A illustrates a simplified example of data storage corresponding to measurements of light intensity for a series of pixels. Light intensity corresponding to a scale, for example, 1–256 may be detected at the image sensor 28. Measurements at each pixel are analyzed to determine if a threshold level of intensity is available for a representative image. For example, light intensity is considered negligible or null N, if the threshold level is set at 128 and the light intensity is measured at less than 128. A light intensity greater than or equal to 128 is meaningful and can be stored in memory. The threshold intensity levels for each light source may be optimized by experimentation. Total light intensity is the combination of intensity associated with the wavelengths of the light sources.

Figure 6B:
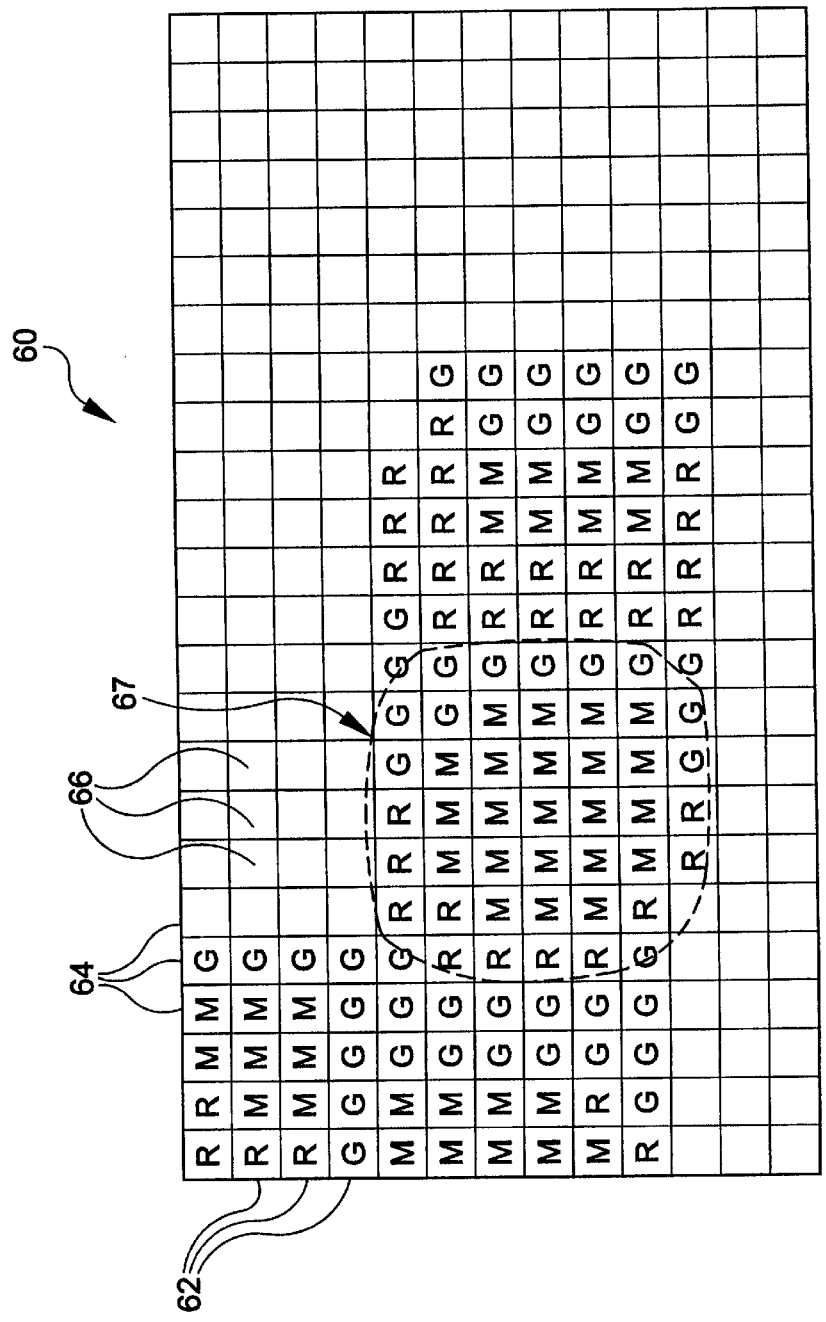
FIG. 6B is a simplified example of a two dimensional matrix representing an image.

FIG. 6B illustrates a simplified example of a two dimensional matrix 60 which can be generated from image sensor 28 to represent an image of a particle. A plurality of rows 62 and columns 64 define color information units 66 for each pixel. A threshold light intensity of red is designated as R; green is designated as G; red and green are designated as M. The image of an individual particle 67 includes M units surrounded by R units and G units. Generally, a greater number of pixels increases the resolution of the image and provides more accurate particle size data.

The image sensor 28 may also include a camera having a black/white CCD. The soil sample may be imaged twice to determine the edges and dimensions of the individual particles. To isolate a first edge of a particle, a first image may be taken with a first light source positioned on a first side of the camera and at an angle, preferably about 45 degrees, relative to the soil sample. To isolate a second edge of the particle, a second image would be taken with a second light source positioned on a second opposed side of the camera and at an angle, preferably about 45 degrees relative to the soil sample. The boundaries of the first and second sides of the particle can be formed by combining the two images. Individual particles boundaries may also be isolated from a single image by isolating areas of low light reflection associated with areas of void spaces between the particles.

FIG. 6C is a simplified example of data storage corresponding to measurements of light intensity for three color sources which may be used to form a color palette representing the image. Total light intensity may be calculated and stored for further analysis.

Figure 7:
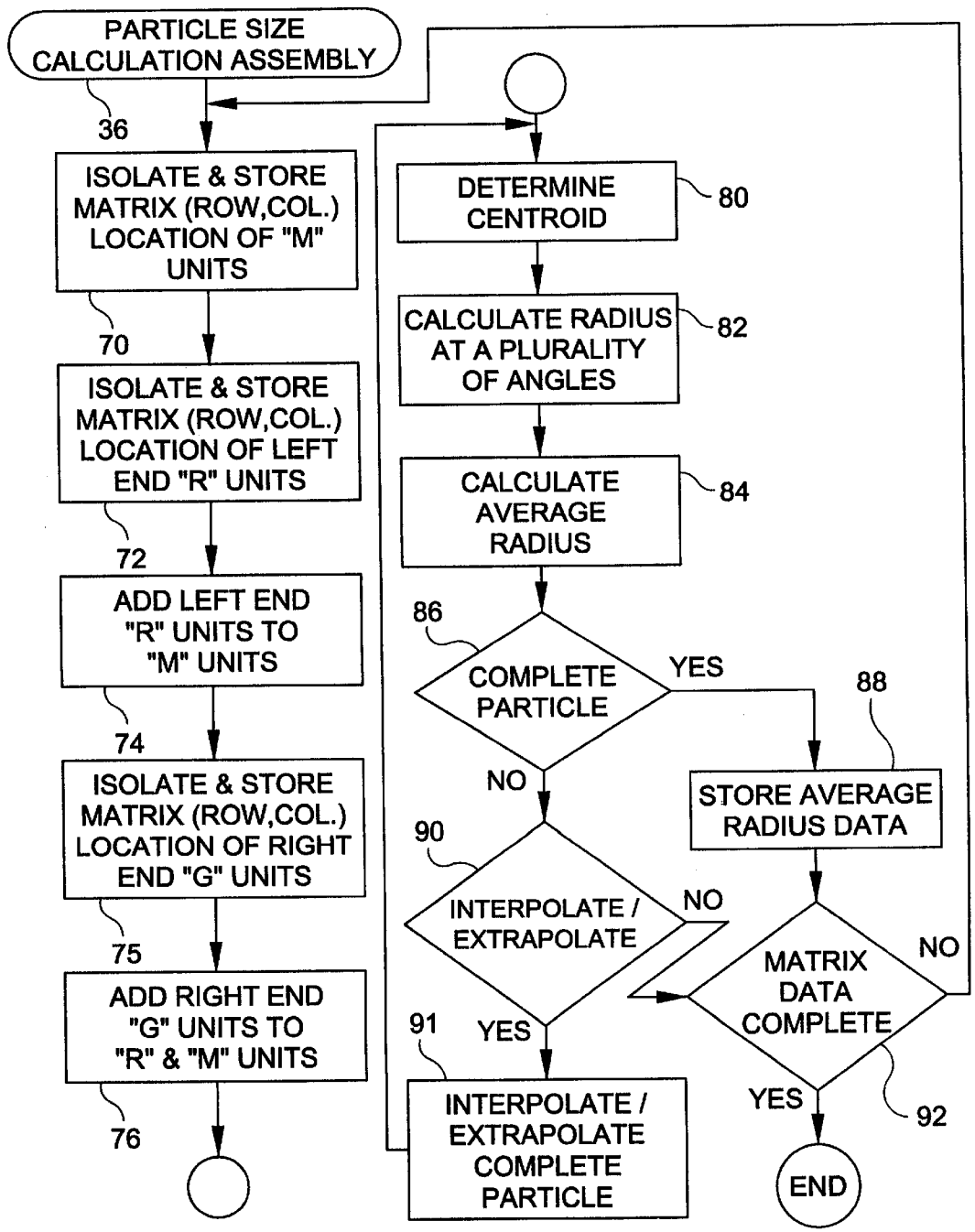
FIG. 7 is a simplified flow chart of software for the soil analysis system.

FIG. 7 illustrates a simplified flow chart of software instructions for isolating particles and determining particle size by the particle size calculation assembly 36. The algorithm instructions are continuously executed, X number of times, until the particle size information for all of the visible particles has been determined. Step 70 isolates M units for a particle. The matrix (row, column) location of all M units is recorded or stored for further analysis.

Steps 72–76 determine the outer boundaries of a particle. For example, the left edge of the particle is determined by isolating R units to the left of the M units. R units generally indicate the boundary of G units. Step 74 adds the R units to the M units. Step 75 determines the right edge limit of a particle by isolating area G units. Step 76 adds the locations of G units to the R units and M units. Once the matrix location information for a particle is complete, step 80 determines a centroid of the particle. Step 82 calculates a radius from the centroid to the perimeter using a plurality of angles. Step 84 determines the average radius of the particle. Additional steps may include performing a statistical analysis to determine whether a radius measurement is consistent with the other calculated radii and if the radius measurement should be included in the data. Step 86 analyzes whether a particle has been isolated or if only a fraction of the particle has been isolated. If the particle has been isolated, the average radius is stored at step 88 for further analysis.

Incomplete particle size data influences the accuracy of the soil analysis results. For example, if step 72 does not isolate R units or if step 76 does not isolate G units, an incomplete particle flag is initiated. Step 90 determines whether the missing portion of the particles or an image of a complete particle can be extrapolated from other available information.

FIG. 8 illustrates an example of particles positioned at different levels. The depth of the particles may be determined to create a three dimensional representation. For example, the right portion of particle A is obstructed by particle B. In this situation, G units may be extrapolated based upon the R units and the M units. To define the particle, the centroid of the combined particle may be determined at step 80; the radius calculated at various angles at step 82; the average radius calculated at step 84; and the average radius may be stored at step 88. Particle size may also be determined by area measurements. The missing portion of the particle may be determined at step 91. Step 92 determines if the matrix data is complete. If all of the matrix data has not been analyzed, steps 70–92 repeat until completion.

FIG. 9 illustrates an example of particles A and C obstructing particle B. Red and green light from the first and second light sources 44, 46 shine at opposed angles on particles A, B, and C. The relative depth of the particles may be determined based upon the angle of incident light and the width of the shadow created. The height of layer may be determined based upon the angle of the incident light and the length of the shadow using trigonometry. Since portions of particle B are hidden, some information may not be available or extrapolated under certain conditions. In such situations, particle B may be excluded from the data.

Figure 10:
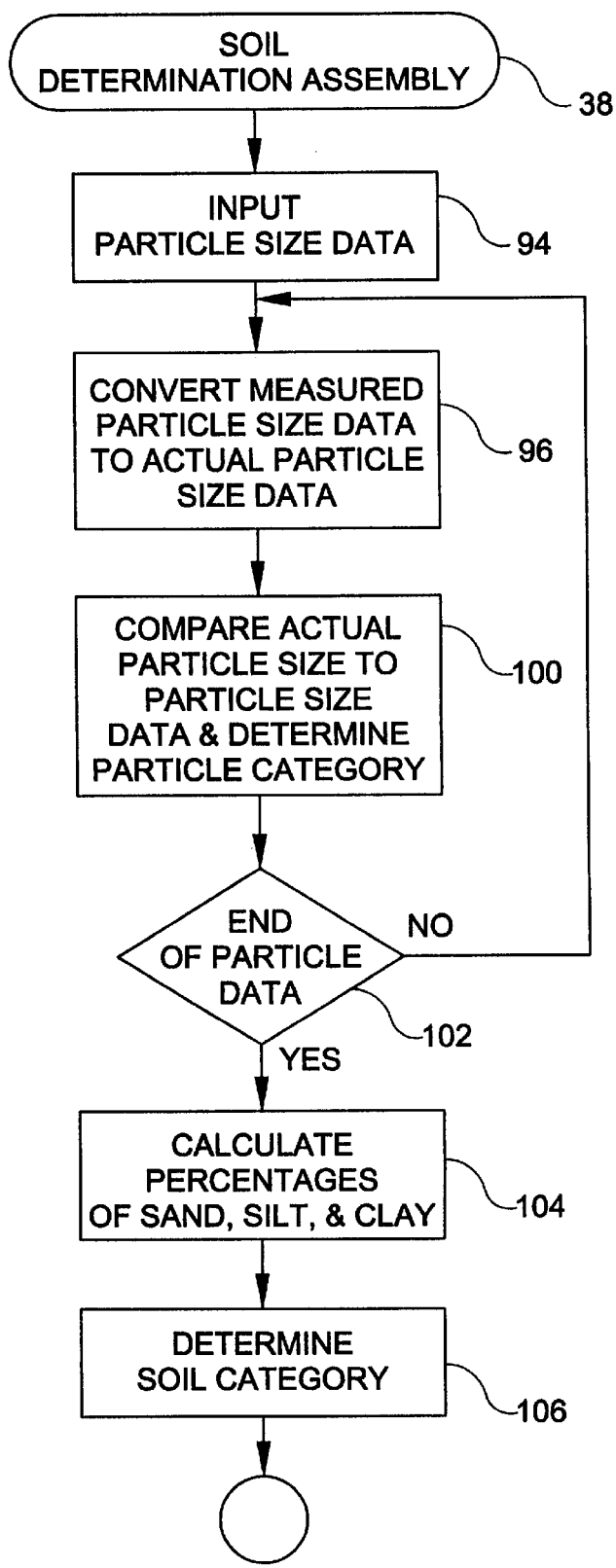
FIG. 10 is a simplified flow chart of software for the soil analysis system.

FIG. 10 illustrates a simplified flow chart of software instructions for determining a category of soil using the soil determination assembly 38. Step 94 inputs data relating to particle size of sand, silt and clay including ranges of particle size determined from experimentation or available soil data. Step 96 uses radius information of a particle for comparison with data relating to particle sizes of sand, silt, and clay. Step 100 compares each individual actual particle dimension to determine if the particle is sand, silt, or clay and stores the information. This process continues until all of the particles have been analyzed. The percentages of sand, silt, and clay in the soil sample are calculated at step 104. The category of soil is determined at step 106. The data is stored in computer memory and further analyzed as desired.

Figure 11:
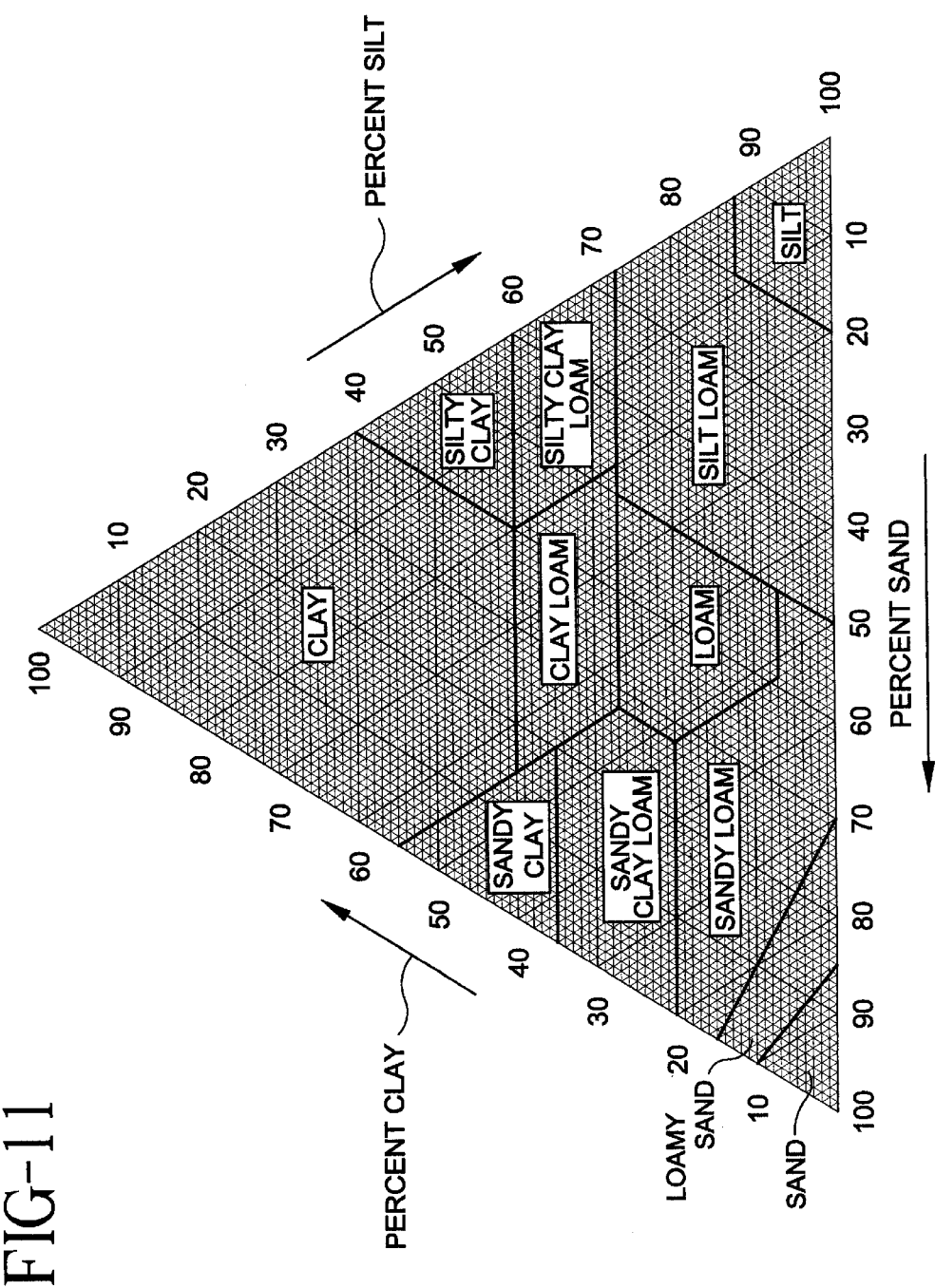
FIG. 11 is a chart identifying categories of soil.

FIG. 11 illustrates a chart from the United States Department of Agriculture categorizing soil based upon the percentage of sand, percentage of silt, and percentage of clay in a soil sample. For example, a soil sample including 20% clay, 40% sand, and 40% silt is classified as loam. An appropriate soil treatment for the field may be determined based on a determination of the categories of soil for each soil sample over a geographic area.

A series of soil samples advantageously allows a user to determine one or more materials, such as fertilizer, seed, or chemical, and the rate of application of the materials to be distributed over a field.

An application treatment map may incorporate geographical maps and field characteristic maps having attributes which affect production and growth. The evaluation and influence of each attribute may be determined based upon agronomic relationships, data, and experimentation. Soil data may include soil nutrient levels, soil pH, and organic matter. A soil map using data from the soil analysis system 12 and a field location system may be prepared by a map generating system.

To coordinate soil information with field location, the field location of the vehicle 10 may be tracked for each soil sample. Field location may be determined by a variety of methods including a Global Positioning System such as a LORAN navigation system for tracking the vehicle by satellites as it moves through the field; or a dead reckoning system for tracking the vehicle based upon a field location relative to a fixed frame of reference which may be adjusted based upon vehicle speed and time. Soil information may be integrated with a geographical information systems (GIS) to provide treatment plans. Reference is made to a geographical information system (GIS) for controlling application of material to a field as described in U.S. Pat. Ser. No. 08/774,627 entitled, System and Method for Creating Agricultural Design and Application Maps for Automated Agricultural Machines. The maps may contain geographical data including field boundaries, waterways, terrain, and field characteristic data.

The soil imaging assembly 24 may be positioned at a forward end of the vehicle 10 for imaging of the soil samples. The particle size calculation assembly 36 and soil determination assembly 38 cooperate to provide soil information that can be incorporated into a GIS system. A corresponding treatment map controls the dispensing apparatus 22 as the vehicle 10 moves through the field. Data collection and treatment of the field may occur at substantially the same time as the vehicle 10 transverses the field.

The soil analysis system 12 may be independent of a field application process. The frequency of soil sample testing may be controlled and adjusted depending upon the field location and topography. For example, a particular area of a field may have more diverse topography and more categories of soil where additional test samples produces a more detailed and accurate soil map. To accomplish the increased test samples in a particular area, the vehicle may increase the number of transverses it makes in a particular area of a field.

The soil analysis assembly 12 may include software including Graphics Interchange Format (GIF) and Tag Image File Format (TIFF) for high-resolution graphics and the interchange of digital image data.

The above described embodiments of the invention are merely descriptive of its principles and are not to be considered limiting. Further modifications of the invention herein disclosed will occur to those skilled in the respective arts and all such modifications are deemed to be within the scope of the invention as defined by the following claims.

What is claimed is:

1. A soil analysis system comprising:

a sensor device configured to produce information corresponding to an image of at least a portion of one or more particles in one or more portions of a soil sample;

an image analysis assembly operatively coupled to the sensor device, the image analysis assembly configured to determine a category for each of the one or mare particles wherein the category is based on a function of size or surface area of the one or more particles; and a first light source positioned at an angle relative to the soil sable on a first side of the sensor device and a second light source positioned at an angle relative to the soil sample on a second side of the sensor device.

2. The soil analysis system of claim 1 wherein the soil analysis system is adapted to determine a category for the one or more portions of the soil sample, the category selected from the group consisting of clay, sandy clay, silty clay, sandy clay loam, clay loam, silty clay loam, sand, loamy sand, sandy loam, loam, and silt.

3. The soil analysis system of claim 1 wherein the image analysis assembly further comprises;

a particle size calculation assembly for determining the size of each of the one or more particles; and a soil determination assembly for determining at least one category of soil for each of the one or more particles.

4. The soil analysis system of claim 3 wherein the particle size calculation assembly is adapted to determine an average radius of the one or more particles.

5. The soil analysis system of claim 3 wherein the particle size calculation assembly determines the centroid of each of the one or more particles.

6. The soil analysis system of claim 5 wherein the particle size calculation assembly further determines the radius from the centroid of each of the one or more particles to the perimeter of each of the one or more particles and further determines the average radius of each of the one or more particles.

7. The soil analysis system of claim 1 wherein the first light source has a first wavelength and the second light source has a second wavelength different from the first wavelength.

8. The soil analysis system of claim 1 wherein the sensor device is adapted to distinguish at least a portion of one or more edges of the one or more particles.

9. The soil analysis system of claim wherein image analysis assembly is adapted to determine if a particle has been substantially isolated.

10. The soil analysis system of claim 9 wherein the image analysis assembly is configured to determine the percentage of sand, silt, and clay in the soil sample and categorize the soil sample.

11. A soil analysis system comprising:
- a soil uncovering device to provide a continuous soil sample stream being representative of a continuous, non discrete, frequency of soil sample testing;
- a sensor device configured to produce information corresponding to an image of at least a portion of one or more particles in the soil sample stream; and
- an image analysis assembly operatively coupled to the sensor device, the image analysis assembly configured to d die a category for the one or more particles wherein the category is based on a function of size or surface area of the one or more particles;
- wherein the image analysis assembly is adapted to determine an average radius of the one or more particles.

12. The soil analysis system of claim 11 wherein the image analysis assembly is configured to compare the size of the one or more particles in the soil sample stream to data relating to sand, silt, and clay and categorize the one or more particles as one of sand, silt, and clay.

13. A soil analysis system comprising:
- a soil imaging assembly to capture an image of a soil sample and isolate individual particles to distinguish individual particles in the soil sample;
- a particle size calculation assembly to analyze the size of individual particles in the soil sample, wherein the particle size calculation assembly is adapted to determine an average radius of each of the one or more particles; and
- a soil determination assembly to compare the size of the individual particles to particular size and to de eh particle characteristic as one of at least sand, silt, and clay.

14. The soil analysis system of claim 13 wherein the soil determination assembly is operatively coupled to a controller for operation of an apparatus for treatment of a geographic area.

15. The soil analysis system of claim 14 wherein the controller functionally cooperates with one or more maps relating to characteristics of a geographic area.

16. The soil analysis system of claim 13 wherein the soil determination assembly is operatively coupled to a mapping system.

17. The soil analysis system of claim 16 wherein the mapping system is configured to integrate one or more soil type maps with one or more data maps.

18. The soil analysis system of claim 13 wherein the soil determination assembly is operatively coupled to a map analysis system configured to analysis one or more data maps.

19. The soil analysis system of claim 13 wherein the soil imaging assembly comprises a soil uncovering device and an image sensor, the soil uncovering device to provide a continuous soil sample stream being representative of a continuous, non discrete, frequency of soil sample testing, and the image sensor to isolate individual particles for the particle size calculation assembly.

20. The soil analysis system of claim 13 wherein the soil determination assembly further calculates a percentage of sand, silt, and clay in the soil sample, and further compares the percentage of sand, silt, and clay to soil data to determine a category of soil for the soil sample.

21. A method of soil analysis comprising the following steps:
- providing a soil sample;
- positioning a sensor device configured to produce information corresponding to an image of at least a portion of one or more particles in the soil sample;
- determining from the image of at least a portion of one or more particles in the soil sample an average radius of each of the one or more particles;
- comparing the average radius of each of the one or more particles to data relating to at least one of sand, silt, and clay.

22. The method of soil analysis of claim 21 further comprising the steps of:
- classifying each of the one or more particles as one of sand, silt, and clay; and
- determining the percentage of the sand, silt, and clay in the soil sample.

\* \* \* \* \*